United States Patent [19]

Scherkenbeck et al.

[11] Patent Number: 5,525,591
[45] Date of Patent: Jun. 11, 1996

[54] ENDOPARASITICIDAL COMPOSITIONS BASED ON OPEN-CHAIN OCTADEPSIPEPTIDES

[75] Inventors: Jürgen Scherkenbeck, Wermelskirchen; Peter Jeschke, Leverkusen; Andrew Plant, Odenthal; Achim Harder, Köln; Norbert Mencke, Leverkusen, all of Germany

[73] Assignee: Bayer Aktiengesellschaft, Leverkusen, Germany

[21] Appl. No.: 347,628

[22] Filed: Dec. 1, 1994

[30] Foreign Application Priority Data

Dec. 9, 1993 [DE] Germany .................. 43 41 993.3

[51] Int. Cl.⁶ .................. A61K 38/15; C07K 11/00
[52] U.S. Cl. .................. 514/18; 530/323; 530/330; 930/30
[58] Field of Search .................. 514/16, 18; 930/30; 530/323, 328, 330

[56] References Cited

FOREIGN PATENT DOCUMENTS

| | | |
|---|---|---|
| 0626376 | 11/1994 | European Pat. Off. . |
| 0626375 | 11/1994 | European Pat. Off. . |
| 320148 | 12/1993 | Japan . |

OTHER PUBLICATIONS

H. G. Lerchen & H. Kunz: Tetrahedron Lett. 26 (43) pp. 5257–5260 (1985).
H. G. Lerchen & H. Kunz: Tetrahedron Lett. 28 (17) pp. 1873–1876 (1987).
B. F. Gisin: Helv. Chim. Acta 56 pp. 1476–1482 (1973).
R. Bowman et al: J. Chem. Soc. pp. 1346–1349 (1950).
J. R. McDermott et al: Can. J. Chem. 51 pp. 1915–1919 (1973).
E. Wurziger et al: Kontake [Catalysts] (Merck Darmstadt) 3 pp. 8–11 (1987).
S. M. Birnbaum et al: J. Amer. Chem. Soc. pp. 6054–6058 (1954).
C. S. Rondestvedt et al: Org. Reactions 11 pp. 189–260 (1960).
Chemical Abstracts: Amino Acids, Peptides, Proteins vol. 121, 1994 p. 1247.
Tetrahedron Letters, No. 46, issued 1977, Kanaoka et al, "Synthesis of Bassianolide", pp. 4049–4050.

*Primary Examiner*—Jeffrey E. Russel
*Attorney, Agent, or Firm*—Sprung Horn Kramer & Woods

[57] ABSTRACT

The present invention relates to the use of open-chain octadepsipeptides of the general formula (I)

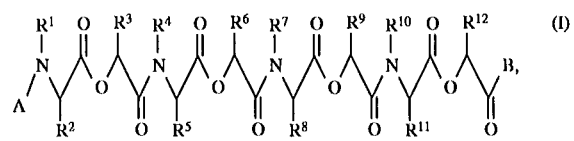

which are used for combating endoparsites in medicine and veterinary medicine.

2 Claims, No Drawings

ENDOPARASITICIDAL COMPOSITIONS BASED ON OPEN-CHAIN OCTADEPSIPEPTIDES

The present invention relates to the use of open-chain octadepsipeptides for combatting endoparasites.

Certain open-chain octadepsipeptides as starting substances for endoparasiticidally active cyclic depsipeptides having 24 ring atoms are the subject-matter of earlier, but not prior-published, patent applications (German Patent Application P 4 317 457.4; P 4 317 432.9).

Nothing is known about a use of these compounds against endoparasites.

It has now been found that the open-chain octadepsipeptides of the general formula (I)

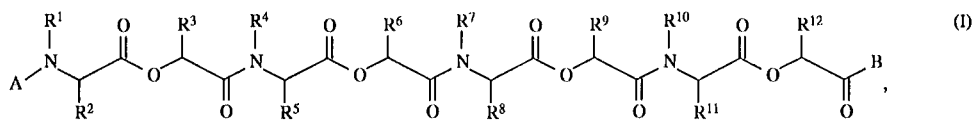

in which

A represents hydrogen, alkyl, aralkyl or an acyl radical, in particular a radical of the formula —CO—R$^{16}$ in which R$^{15}$ represents straight-chain or branched alkyl, alkenyl, alkoxy, aralkyl or arylalkoxy having up to 6 carbon atoms in the alkyl moiety, R$^1$, R$^4$, R$^7$ and R$^{10}$ independently of one another represent C$_1$–C$_8$-alkyl, C$_3$–C$_6$-cycloalkyl or aralkyl, R$^2$, R$^5$, R$^8$ and R$^{11}$ independently of one another represent hydrogen, straight-chain or branched alkyl having up to 8 carbon atoms, hydroxyalkyl, alkanoyloxyalkyl, alkoxyalkyl, aryloxyalkyl, mercaptoalkyl, alkylthioalkyl, alkylsulphinylalkyl, alkylsulphonylalkyl, carboxyalkyl, alkoxycarbonylalkyl, arylalkoxycarbonylalkyl, carbamoylalkyl, aminoalkyl, alkylaminoalkyl, dialkylaminoalkyl, guanidinoalkyl, which can optionally be substituted by one or two benzyloxycarbonyl radicals or by one, two, three or four alkyl radicals, or represent alkoxycarbonylaminoalkyl, 9-fluorenylmethoxycarbonyl (Fmoc) aminoalkyl, alkenyl, cycloalkyl, cycloalkylalkyl and optionally substituted arylalkyl, substituents which may be mentioned being halogen, hydroxyl, alkyl and alkoxy, R$^3$, R$^6$, R$^9$ and R$^{12}$ independently of one another represent hydrogen, straight-chain or branched alkyl having up to 8 carbon atoms, hydroxyalkyl, alkanoyloxyalkyl, alkoxyalkyl, aryloxyalkyl, alkylthioalkyl, alkylsulphinylalkyl, alkylsulphonylalkyl, carboxyalkyl, alkoxycarbonylalkyl, arylalkoxycarbonylalkyl, carbamoylalkyl, aminoalkyl, alkylaminoalkyl, dialkylaminoalkyl, alkoxycarbonylaminoalkyl, alkenyl, cycloalkyl, cycloalkylalkyl, hetaryl, aralkyl, heteroarylmethyl or arylalkyl which may be substituted by halogen, hydroxyl, C$_1$–C$_4$-alkyl, C$_1$–C$_4$-alkoxy, nitro or a NR$^{16}$R$^{17}$ group in which R$^{16}$ and R$^{17}$ independently from each other represent hydrogen or alkyl or together with the adjoining nitrogen form a 5, 6 or 7-membered ring which is optionally interrupted by O, S or H and which is optionally C$_{1\text{-}4}$-alkyl substituted, B represents hydroxyl, alkoxy having up to 4 carbon atoms or the radical NR$^{13}$R$^{14}$ in which R$^{13}$ and R$^{14}$ represent hydrogen, alkyl, aralkyl or aryl, and their optical isomers and racemates, can be used in medicine and veterinary medicine for combating endoparasites.

Formula (I) provides a general definition of the open-chain octadepsipeptides to be used according to the invention.

In the general formulae, alkyl denotes straight-chain or branched alkyl having preferably 1 to 9 carbon atoms, particularly preferably 1 to 5, and very particularly preferably 1 to 4, carbon atoms. The following may be mentioned by way of example: methyl, ethyl, n- and i-propyl, n-, i-, s- and t-butyl, pentyl, hexyl and octyl which are optionally substituted.

In the general formulae alkenyl denotes straight-chain or branched alkenyl having preferably 2 to 20, particularly 2 to 8 carbon atoms. The following may be mentioned by way of example: ethenyl, propenyl-(1), propenyl-(2), butenyl-(3) which are optionally substituted.

In the general formulae cycloalkyl denotes mono-, bi- or tricyclic cycloalkyl having preferably 3 to 10, particularly 3, 5 or 6 ring carbon atoms. The following may be mentioned by way of example: cyclopropyl, cyclobutyl, cyclopentyl, cyclohexyl, cycloheptyl which are optionally substituted.

Alkoxy in the general formulae is straight-chain or branched alkoxy having preferably 1 to 6, in particular 1 to 4, carbon atoms. Methoxy, ethoxy, propoxy, butoxy and their isomers, such as, for example, i-propoxy, and i-, s- and t-butoxy, may be mentioned by way of example, and may be substituted.

Alkylthio in the general formulae is straight-chain or branched alkylthio having preferably 1 to 6, particularly preferably 1 to 4, carbon atoms, for example optionally substituted methylthio, ethylthio, propylthio, butylthio, pentylthio and their isomers, such as, for example, i-propylthio, i-, s- and t-butylthio. Halogenoalkyl in the general formulae has 1 to 4, particularly 1 or 2 carbon-atoms and 1 to 9, particularly 1 to 5 same or different halogen atoms. As halogen atoms are mentioned fluorine, chlorine. The following may be mentioned by way of example trifluoromethyl, chloro-difluoromethyl, 2,2,2-trifluoroethyl, pentafluoroethyl, perfluoro-t-butyl.

Aryl in the general formulae is aryl having preferably 6 or 10 carbon atoms in the aryl moiety. Unsubstituted or substituted phenyl or naphthyl, in particular phenyl, may be mentioned as being preferred and may be substituted.

Arylalkyl in the general formulae is optionally substituted in the alkyl- or in the aryl part, it has preferably 6 or 10, particularly 6 carbon atoms in the aryl part, mention being made of naphthyl and phenyl, very particularly mentioned is phenyl, in the alkyl part 1 to 4 carbon atoms, particularly 1 or 2 carbon atoms may be mentioned. Benzyl or phenethyl may be mentioned by way of example.

Heteroaryl in the general formulae is preferably a 5 to 7-membered heteroaromatic, optionally benzo-fused ring which contains one or more hetero atoms, preferably 1 to 3 identical or different hetero atoms. Preferred hetero atoms which may be mentioned are oxygen, sulphur and nitrogen. The following may be mentioned as particularly preferred for heteroaryl: pyridyl, pyrimidinyl, pyridazinyl, pyrazinyl, furyl, thienyl, pyrazolyl, imidazolyl, triazolyl, isoxazolyl, isothiazolyl, pyrrolyl, piperazinyl, triazinyl, oxazinyl, oxepinyl, thiepinyl, diazepinyl, thiazolyl, thiadiazolyl, oxadiazolyl, oxazolyl, quinolyl, isoquinolyl, benzoxazolyl, benzothiazolyl and benzimidazolyl. The heteroaryl ring can itself be substituted. In the general formulae optionally substituted radicals may carry one or more, preferably 1 to 3, particularly 1 to 2 same or different substituents. The following substituents may be mentioned as examples:

Alkyl with preferably 1 to 4 particularly 1 to 2 carbon atoms, methyl, ethyl, n- and i-propoyl, n-, i- and t-butyl are named as examples; alkoxy with preferably 1 to 4 particularly 1 to 2 carbon atoms, methoxy, ethoxy, n- or i-propoxy, n-, i- or t-butoxy are named as examples; alkylthio with preferably 1 to 4 particularly 1 to 2 carbon atoms, methylthio, ethylthio, n- or i-propylthio, n-, i- or t-butylthio are named as examples; alkylsulfinyl or alkylsulfonyl with preferably 1 to 4 particularly 1 to 2 carbon atoms like methylsulfinyl, methylsulfonyl, ethylsulfinyl, ethylsulfonyl; arylsulfonyl with 6 to 10 carbon atoms in the aryl part like phenylsulfonyl; halogenoalkyl, halogenoalkoxy, halogenoalkylthio, halogenoalkylsulphinyl and/or halogenoalkylsulphonyl (having in each case preferably 1 to 4, in particular 1 to 2, carbon atoms and in each case 1 to 6, in particular 1 to 3, identical or different halogen atoms, in particular fluorine and/or chlorine atoms), trifluormethyl, difluormethyl, trifluormethylsulfinyl, trifluormethylsulfonyl, perfluor n, s, t-butylsulfonyl may be mentioned by way of example. Further substituents which may be mentioned are hydroxy, halogen preferably fluorine, chlorine, cyano, nitro, amino, formimino

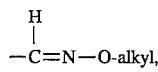

mono- or dialkylamino having 1 or 2 alkyl groups, each of which can be straight-chain or branched and contain preferably 1 to 5, in particular 1 to 4 and particularly preferably 1 to 3, carbon atoms, mention being made of methyl, ethyl and n- and i-propyl; dimethylamino, diethylamino, di-n-propylamino and di-i-propylamino may be mentioned by way of example; further substituents which may be mentioned are acyl, aryl, aryloxy, heteroaryl, heteroarylalkyl, heteroaryloxy which may be substituted themselves by one of the above mentioned substituents.

Compounds of the formula (I) which are preferably used according to the invention are those in which A represents hydrogen, $C_1$–$C_4$-alkyl or benzyl, or represents a group of the formula —CO—$R^{15}$ in which $R^{15}$ represents straight-chain or branched $C_1$–$C_4$-alkyl, $C_2$–$C_4$-alkenyl, $C_1$–$C_4$-alkoxy or phenylalkoxy having up to 6 carbon atoms in the alkyl moiety, in particular tert-butoxy, benzyloxy, ethoxy, allyloxy, fluorenyl-9-methoxy or methoxy, $R^1$, $R^4$, $R^7$ and $R^{10}$ independently of one another represent $C_1$–$C_4$-alkyl, $C_3$–$C_6$-cycloalkyl, phenyl-$C_{1-4}$-alkyl, $R^2$, $R^5$, $R^8$ and $R^{11}$ independently of one another represent hydrogen, straight-chain or branched $C_{1-8}$-alkyl, in particular methyl, ethyl, propyl, isopropyl, butyl, isobutyl, sec-butyl, tert-butyl, pentyl, isopentyl, sec-pentyl, hexyl, isohexyl, sec-hexyl, heptyl, isoheptyl, sec-heptyl, tert-heptyl, octyl, isooctyl, sec-octyl, hydroxy-$C_1$–$C_6$-alkyl, in particular hydroxymethyl, 1-hydroxyethyl, $C_1$–$C_4$-alkanoyloxy-$C_1$–$C_6$-alkyl, in particular acetoxymethyl, 1-acetoxyethyl, $C_1$–$C_4$-alkoxy-$C_1$–$C_6$-alkyl, in particular methoxymethyl, 1-methoxyethyl, aryl-$C_1$–$C_4$-alkyloxy-$C_1$–$C_6$-alkyl, in particular benzyloxymethyl, 1-benzyloxyethyl, mercapto-$C_1$–$C_6$-alkyl, in particular mercaptomethyl, $C_1$–$C_4$-alkylthio-$C_1$–$C_6$-alkyl, in particular methylthioethyl, $C_1$–$C_4$-alkylsulphinyl-$C_1$–$C_6$-alkyl, in particular methylsulphinylethyl, $C_1$–$C_4$-alkylsulphonyl-$C_1$–$C_6$-alkyl, in particular methylsulphonylethyl, carboxy-$C_1$–$C_6$-alkyl, in particular carboxymethyl, carboxyethyl, $C_1$–$C_4$-alkoxycarbonyl-$C_1$–$C_6$-alkyl, in particular methoxycarbonylmethyl, ethoxycarbonylethyl, $C_1$–$C_4$-arylalkoxycarbonyl-$C_1$–$C_6$-alkyl, in particular benzyloxycarbonylmethyl, carbamoyl-$C_1$–$C_6$-alkyl, in particular carbamoylmethyl, carbamoylethyl, amino-$C_1$–$C_6$-alkyl, in particular aminopropyl, aminobutyl, $C_1$–$C_4$-alkylamino-$C_1$–$C_6$-alkyl, in particular methylaminopropyl, methylaminobutyl, $C_1$–$C_4$-dialkylamino-$C_1$–$C_6$-alkyl, in particular dimethylaminopropyl, dimethylaminobutyl, guanido-$C_1$–$C_6$-alkyl, in particular guanidopropyl, $C_1$–$C_4$-alkoxycarbonylamino-$C_1$–$C_6$-alkyl, in particular tert-butoxycarbonylaminopropyl, tert-butoxycarbonylaminobutyl, 9-fluorenylmethoxycarbonyl (Fmoc) aminopropyl, 9-fluorenylmethoxycarbonyl (Fmoc) aminobutyl, $C_2$–$C_8$-alkenyl, in particular vinyl, allyl, butenyl, $C_3$–$C_7$-cycloalkyl, in particular cyclopentyl, cyclohexyl, cycloheptyl, $C_3$–$C_7$-cycloalkyl-$C_1$–$C_4$-alkyl, in particular cyclopentylmethyl, cyclohexylmethyl, cycloheptylmethyl, phenyl-$C_1$–$C_4$-alkyl, in particular phenylmethyl, which can optionally be substituted by radicals from the series comprising halogen, in particular fluorine, chlorine, bromine or iodine, hydroxyl, $C_1$–$C_4$-alkoxy, in particular methoxy or ethoxy, $C_1$–$C_4$-alkyl, in particular methyl, $R^3$, $R^6$, $R^9$ and $R^{12}$ independently of one another represent hydrogen, straight-chain or branched $C_1$–$C_8$-alkyl, in particular methyl, ethyl, propyl, isopropyl, butyl, isobutyl, sec-butyl, tert-butyl, pentyl, isopentyl, sec-pentyl, hexyl, isohexyl, sec-hexyl, heptyl, isoheptyl, sec-heptyl, tert-heptyl, octyl, isooctyl, sec-octyl, hydroxy-$C_1$–$C_6$-alkyl, in particular hydroxymethyl, 1-hydroxyethyl, $C_1$–$C_4$-alkanoyloxy-$C_1$–$C_6$-alkyl, in particular acetoxymethyl, 1-acetoxyethyl, $C_1$–$C_4$-alkoxy-$C_1$–$C_6$-alkyl, in particular methoxymethyl, 1-methoxyethyl, aryl-$C_1$–$C_4$-alkyloxy-$C_1$–$C_6$-alkyl, in particular benzyloxymethyl, 1-benzyloxyethyl, mercapto-$C_1$–$C_6$-alkyl, in particular mercaptomethyl, $C_1$–$C_4$-alkylthio-$C_1$–$C_6$-alkyl, in particular methylthioethyl, $C_1$–$C_4$-alkylsulphinyl-$C_1$–$C_6$-alkyl, in particular methylsulphinylethyl, $C_1$–$C_4$-alkylsulphonyl-$C_1$–$C_6$-alkyl, in particular methylsulphonylethyl, carboxy-$C_1$–$C_6$-alkyl, in particular carboxymethyl, carboxyethyl, $C_1$–$C_4$-alkoxycarbonyl-$C_1$–$C_6$-alkyl, in particular methoxycarbonylmethyl, ethoxycarbonylethyl, $C_1$–$C_4$-arylalkoxycarbonyl-$C_1$–$C_6$-alkyl, in particular benzyloxycarbonylmethyl, carbamoyl-$C_1$–$C_6$-alkyl, in particular carbamoylmethyl, carbamoylethyl, amino-$C_1$–$C_6$-alkyl, in particular aminopropyl, aminobutyl, $C_1$–$C_4$-alkylamino-$C_1$–$C_6$-alkyl, in particular methylaminopropyl, methylaminobutyl, $C_1$–$C_4$-dialkylamino-$C_1$–$C_6$-alkyl, in particular dimethylaminopropyl, dimethylaminobutyl, guanido-$C_1$–$C_6$-alkyl, in particular guanidopropyl, $C_1$–$C_4$-alkoxycarbonylamino-$C_1$–$C_6$-alkyl, in particular tert-butoxycarbonylaminopropyl, tert-butoxycarbonylaminobutyl, 9-fluorenylmethoxycarbonyl(Fmoc)aminopropyl, 9-fluorenylmethoxycarbonyl(Fmoc)aminobutyl, $C_2$–$C_8$-alkenyl, in particular vinyl, allyl, butenyl, $C_3$–$C_7$-cycloalkyl, in particular cyclopentyl, cyclohexyl, cycloheptyl, $C_3$–$C_7$-cycloalkyl-$C_1$–$C_4$-alkyl, in particular cyclopentylmethyl, cyclohexylmethyl, cycloheptylmethyl, and furthermore represents aryl, hetaryl, aralkyl or heteroarylmethyl which may be substituted by halogen, hydroxyl, $C_{1-4}$-alkyl, $C_{1-4}$-alkoxy, nitro or a $NR^{16}R^{17}$ group in which $R^{16}$ and $R^{17}$ independently from each other represent hydrogen or alkyl or together with the adjoining nitrogen atom forms a 5, 6 or 7-membered ring which is optionally interrupted by O, S or N and which is optionally $C_{1-4}$-alkyl substituted, B represents hydroxyl, tert-butoxy or the radical $NR^{13}R^{14}$, in which $R^{13}$ and $R^{14}$ independently of one another represent hydrogen, straight-chain or branched $C_{1-4}$-alkyl, in particular methyl, ethyl, isopropyl, t-butyl, benzyl, cyclopropyl, cyclohexyl and phenyl, and their optical isomers and racemates.

Compounds which are particularly preferred according to the invention are those of the formula (I) in which A represents hydrogen, benzyl or a group $COR^{15}$, $R^{15}$ represents straight-chain or branched alkoxy or arylalkoxy having up to 6 carbon atoms in the alkyl moiety, in particular tert-butoxy or benzyloxy, $R^1$, $R^4$, $R^7$ and $R^{10}$ independently of one another represent $C_{1-4}$-alkyl, $C_{3-6}$-cycloalkyl and benzyl, $R^2$, $R^5$, $R^8$ and $R^{11}$ independently of one another represent hydrogen, straight-chain or branched $C_1$–$C_8$-alkyl, in particular methyl, ethyl, propyl, isopropyl, butyl, isobutyl, sec-butyl, pentyl, isopentyl, sec-pentyl, hexyl, isohexyl, sec-hexyl, heptyl, isoheptyl, sec-heptyl, octyl, isooctyl, sec-octyl, hydroxy-$C_1$–$C_4$-alkanoyloxy-$C_1$–$C_6$-alkyl, in particular acetoxymethyl, 1-acetoxyethyl, $C_1$–$C_4$-alkoxy-$C_1$–$C_6$-alkyl, in particular methoxymethyl, 1-methoxyethyl, aryl-$C_1$–$C_4$-alkyloxy-$C_1$–$C_6$-alkyl, in particular benzyloxymethyl, 1-benzyloxyethyl, $C_1$–$C_4$-alkoxycarbonylamino-$C_1$–$C_6$-alkyl, in particular tert-butoxycarbonylaminopropyl, tert-butoxycarbonylaminobutyl, $C_2$–$C_8$-alkenyl, in particular vinyl, allyl, $C_3$–$C_7$-cycloalkyl, in particular cyclopentyl, cyclohexyl, cycloheptyl, $C_3$–$C_7$-cycloalkyl-$C_1$–$C_4$-alkyl, in particular cyclopentylmethyl, cyclohexylmethyl, cycloheptylmethyl, phenyl-$C_1$–$C_4$-alkyl, in particular phenylmethyl, which can optionally be substituted by one or more identical or different radicals from amongst those mentioned above, $R^3$, $R^6$, $R^9$ and $R^{12}$ independently of one another represent hydrogen, straight-chain or branched $C_1$–$C_8$-alkyl, in particular methyl, ethyl, propyl, isopropyl, butyl, isobutyl, sec-butyl, pentyl, isopentyl, sec-pentyl, hexyl, isohexyl, sec-hexyl, heptyl, isoheptyl, sec-heptyl, octyl, isooctyl, sec-octyl, hydroxy-$C_1$–$C_4$-alkanoyloxy-$C_1$–$C_6$-alkyl, in particular acetoxymethyl, 1-acetoxyethyl, $C_1$–$C_4$-alkoxy-$C_1$–$C_6$-alkyl, in particular methoxymethyl, 1-methoxyethyl, aryl-$C_1$–$C_4$-alkyloxy-$C_1$–$C_6$-alkyl, in particular benzyloxymethyl, 1-benzyloxyethyl, $C_1$–$C_4$-alkoxycarbonylamino-$C_1$–$C_6$-alkyl, in particular tert-butoxycarbonylaminopropyl, tert-butoxycarbonylaminobutyl, $C_2$–$C_8$-alkenyl, in particular vinyl, allyl, $C_3$–$C_7$-cycloalkyl, in particular cyclopentyl, cyclohexyl, cycloheptyl, $C_3$–$C_7$-cycloalkyl-$C_1$–$C_4$-alkyl, in particular cyclopentylmethyl, cyclohexylmethyl, cycloheptylmethyl, and furthermore represents aryl, hetaryl, aralkyl or heteroarylmethyl which may be substituted by halogen, hydroxyl, $C_{1-4}$-alkyl, $C_{1-4}$-alkoxy, nitro or a $NR^{16}R^{17}$ group in which $R^{16}$ and $R^{17}$ independently from each other represent hydrogen or alkyl or together with the adjoining nitrogen atom forms a 5, 6 or 7-membered ring which is optionally interrupted by O, S or N and which is optionally $C_{1-4}$-alkyl substituted, B represents hydroxyl or tert-butoxy, and their optical isomers and racemates.

Compounds of the formula (I) which are very particularly preferably used according to the invention are those in which A represents hydrogen or benzyl, $R^1$, $R^4$, $R^7$ and $R^{10}$ independently of one another represent methyl, ethyl, propyl and i-propyl, $R^2$, $R^5$, $R^8$ and $R^{11}$ independently of one another represent hydrogen, straight-chain or branched $C_1$–$C_8$-alkyl, in particular methyl, ethyl, propyl, isopropyl, butyl, isobutyl, sec-butyl, pentyl, isopentyl, sec-pentyl, hexyl, isohexyl, sec-hexyl, heptyl, isoheptyl, sec-heptyl, octyl, isooctyl, sec-octyl, $C_2$–$C_8$-alkenyl, in particular allyl, $C_3$–$C_7$-cycloalkyl-$C_1$–$C_4$-alkyl, in particular cyclohexylmethyl, phenyl-$C_1$–$C_4$-alkyl, in particular phenylmethyl, $R^3$, $R^6$, $R^9$ and $R^{12}$ independently of one another represent hydrogen, straight-chain or branched $C_1$–$C_8$-alkyl, in particular methyl, ethyl, propyl, isopropyl, butyl, isobutyl, sec-butyl, pentyl, isopentyl, sec-pentyl, hexyl, isohexyl, sec-hexyl, heptyl, isoheptyl, sec-heptyl, octyl, isooctyl, sec-octyl, $C_2$–$C_8$-alkenyl, in particular vinyl, allyl, $C_3$–$C_7$-cycloalkyl-$C_1$–$C_4$-alkyl, in particular cyclohexylmethyl, and furthermore represents aryl, hetaryl, arylmethyl or heteroarylmethyl which may be substituted by halogen, hydroxyl, $C_{1-2}$-alkyl, $C_{1-2}$-alkoxy, nitro or a $NR^{16}R^{17}$ group in which $R^{16}$ and $R^{17}$ independently from each other represent hydrogen or alkyl or together with the adjoining nitrogen atom forms a 5, 6 or 7-membered ring which is optionally interrupted by O, S or N, B represents hydroxyl or tert-butoxy, and their optical isomers and racemates.

The following compounds of the general formula (I) in which the radicals A and B have the meanings given in table 1 below

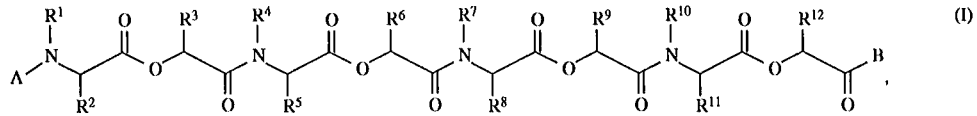

where

Bzl represents benzyl,

Bu represents butyl,

Et represents ethyl,

Me represents methyl and

Pr represents propyl, may be mentioned individually.

TABLE

| Nr. | A | B | $R^1$ | $R^2$ | $R^3$ | $R^4$ | $R^5$ | $R^6$ | $R^7$ | $R^8$ | $R^9$ | $R^{10}$ | $R^{11}$ | $R^{12}$ |
|---|---|---|---|---|---|---|---|---|---|---|---|---|---|---|
| 1 | Bzl | O$^t$Bu | Me | $^i$Bu | Me | Me | $^i$Bu | Bzl | Me | $^i$Bu | Me | Me | $^i$Bu | Bzl |
| 2 | Bzl | H | Me | $^i$Bu | Me | Me | $^i$Bu | Bzl | Me | $^i$Bu | Me | Me | $^i$Bu | Bzl |
| 3 | H | O$^t$Bu | Me | $^i$Bu | Me | Me | $^i$Bu | Bzl | Me | $^i$Bu | Me | Me | $^i$Bu | Bzl |
| 4 | H | OH | Me | $^i$Bu | Me | Me | $^i$Bu | Bzl | Me | $^i$Bu | Me | Me | $^i$Bu | Bzl |
| 5 | Bzl | O$^t$Bu | Me | $^s$Bu | Me | Me | $^s$Bu | Bzl | Me | $^s$Bu | Me | Me | $^s$Bu | Bzl |
| 6 | Bzl | OH | Me | $^s$Bu | Me | Me | $^s$Bu | Bzl | Me | $^s$Bu | Me | Me | $^s$Bu | Bzl |
| 7 | H | OH | Me | $^s$Bu | Me | Me | $^s$Bu | Bal | Me | $^s$Bu | Me | Me | $^s$Bu | Bzl |
| 8 | Bzl | O$^t$Bu | Me | $^i$Pr | Me | Me | $^i$Pr | Bzl | Me | $^i$Pr | Me | Me | $^i$Pr | Bzl |
| 9 | Bzl | OH | Me | $^i$Pr | Me | Me | $^i$Pr | Bzl | Me | $^i$Pr | Me | Me | $^i$Pr | Bzl |
| 10 | H | OH | Me | $^i$Pr | Me | Me | $^i$Pr | Bzl | Me | $^i$Pr | Me | Me | $^i$Pr | Bzl |
| 11 | Bzl | O$^t$Bu | Me | Bzl | Me | Me | Bzl | Bzl | Me | Bzl | Me | Me | Bzl | Bzl |
| 12 | Bzl | Oh | Me | Bzl | Me | Me | Bzl | Bzl | Me | Bzl | Me | Me | Bzl | Bzl |
| 13 | H | OH | Me | Bzl | Me | Me | Bzl | Bzl | Me | Bzl | Me | Me | Bzl | Bzl |
| 14 | Bzl | O$^t$Bu | Me | Me | Me | Me | Me | Bzl | Me | Me | Me | Me | Me | Bzl |
| 15 | Bzl | Oh | Me | Me | Me | Me | Me | Bzl | Me | Me | Me | Me | Me | Bzl |
| 16 | H | OH | Me | Me | Me | Me | Me | Bzl | Me | Me | Me | Me | Me | Bzl |
| 17 | Bzl | O$^t$Bu | Me | Pr | Me | Me | $^i$Bu | Bzl | Me | $^i$Bu | Me | Me | $^i$Bu | Bzl |
| 18 | Bzl | OH | Me | Pr | Me | Me | $^i$Bu | Bzl | Me | $^i$Bu | Me | Me | $^i$Bu | Bzl |
| 19 | H | OH | Me | Pr | Me | Me | $^i$Bu | Bzl | Me | $^i$Bu | Me | Me | $^i$Bu | Bzl |
| 20 | Bzl | O$^t$Bu | Me | H | Me | Me | H | Bzl | Me | $^i$Bu | Me | Me | $^i$Bu | Bzl |
| 21 | Bzl | OH | Me | H | Me | Me | H | Bzl | Me | $^i$Bu | Me | Me | $^i$Bu | Bzl |
| 22 | H | OH | Me | H | Me | Me | H | Bzl | Me | $^i$Bu | Me | Me | $^i$Bu | Bzl |
| 23 | Bzl | O$^t$Bu | Me | Me | Me | Me | Me | Bzl | Me | $^i$Bu | Me | Me | $^i$Bu | Bzl |
| 24 | Bzl | OH | Me | Me | Me | Me | Me | Bzl | Me | $^i$Bu | Me | Me | $^i$Bu | Bzl |
| 25 | H | OH | Me | Me | Me | Me | Me | Bzl | Me | $^i$Bu | Me | Me | $^i$Bu | Bzl |
| 26 | Bzl | O$^t$Bu | Me | $^i$Bu | Me | Me | $^i$Bu | Bzl | Me | $^i$Bu | Me | Me | $^i$Bu | p-Cl—Bzl |
| 27 | Bzl | OH | Me | $^i$Bu | Me | Me | $^i$Bu | Bzl | Me | $^i$Bu | Me | Me | $^i$Bu | p-Cl—Bzl |
| 28 | H | OH | Me | $^i$Bu | Me | Me | $^i$Bu | Bzl | Me | $^i$Bu | Me | Me | $^i$Bu | p-Cl—Bzl |
| 29 | Bzl | O$^t$Bu | Me | $^i$Bu | Me | Me | $^i$Bu | p-Cl—Bzl | Me | $^i$Bu | Me | Me | $^i$Bu | p-Cl—Bzl |
| 30 | Bzl | OH | Me | $^i$Bu | Me | Me | $^i$Bu | p-Cl—Bzl | Me | $^i$Bu | Me | Me | $^i$Bu | p-Cl—Bzl |
| 31 | H | OH | Me | $^i$Bu | Me | Me | $^i$Bu | p-Cl—Bzl | Me | $^i$Bu | Me | Me | $^i$Bu | p-Cl—Bzl |
| 32 | Bzl | O$^t$Bu | Et | $^i$Bu | Me | Et | $^i$Bu | Bzl | Et | $^i$Bu | Me | Et | $^i$Bu | Bzl |
| 33 | Bzl | OH | Et | $^i$Bu | Me | Et | $^i$Bu | Bzl | Et | $^i$Bu | Me | Et | $^i$Bu | Bzl |
| 34 | H | OH | Et | $^i$Bu | Me | Et | $^i$Bu | Bzl | Et | $^i$Bu | Me | Et | $^i$Bu | Bzl |
| 35 | Bzl | O$^t$Bu | Pr | $^i$Bu | Me | Pr | $^i$Bu | Bzl | Pr | $^i$Bu | Me | Pr | $^i$Bu | Bzl |
| 36 | Bzl | OH | Pr | $^i$Bu | Me | Pr | $^i$Bu | Bzl | Pr | $^i$Bu | Me | Pr | $^i$Bu | Bzl |
| 37 | H | OH | Pr | $^i$Bu | Me | Pr | $^i$Bu | Bzl | Pr | $^i$Bu | Me | Pr | $^i$Bu | Bzl |
| 38 | Bzl | O$^t$Bu | $^i$Pr | $^i$Bu | Me | $^i$Pr | $^i$Bu | Bzl | $^i$Pr | $^i$Bu | Me | $^i$Pr | $^i$Bu | Bzl |
| 39 | Bzl | OH | $^i$Pr | $^i$Bu | Me | $^i$Pr | $^i$Bu | Bzl | $^i$Pr | $^i$Bu | Me | $^i$Pr | $^i$Bu | Bzl |
| 40 | H | OH | $^i$Pr | $^i$Bu | Me | $^i$Pr | $^i$Bu | Bzl | $^i$Pr | $^i$Bu | Me | $^i$Pr | $^i$Bu | Bzl |

The compounds of the general formula (I) can exist in optically active, stereoisomeric forms or in the form of racemic mixtures. However, the optically active forms of the compounds of the general formula (I) are preferably used.

The preparation of the open-chain octadepsipeptides of the general formula (I) to be used according to the invention is described in earlier, but not prior-published, patent applications (cf. German Patent Publications P 4 317 457.4; P 4 317 432.9).

The compounds of the formula (I)

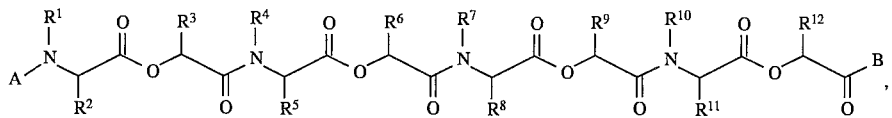

in which

A, $R^1$ to $R^{12}$ and B have the meaning given further above are obtained, for example, when tetradepsipeptides of the general formula (IIa)

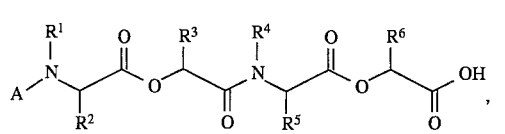

in which

A, and $R^1$ to $R^6$ have the abovementioned meaning are reacted with tetradepsipeptides of the general formula (IIIa)

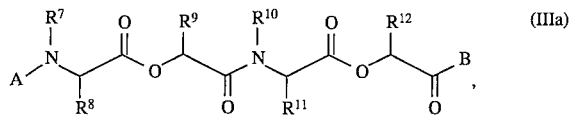

in which $R^7$ to $R^{12}$ have the meaning given further above in the presence of suitable coupling reagents, in the presence of a basic reaction auxiliary and in the presence of a diluent.

The open-chain octadepsipeptides of the formula (I) can be prepared by traditional processes, for example the process described by H.-G. Lerchen and H. Kunz (Tetrahedron Lett. 26 (43) (1985) p. 5257–5260; 28 (17) (1987) p. 1873–1876) which makes use of the esterification method described by B. F. Gisin (Helv. Chim. Acta 56 (1973) p. 1476).

Some of the N-methyl-amino acids and 2-halogeno-carboxylic acid derivatives used as starting materials for the preparation of the compounds of the formulae (IIa) and (IIIa) are known (cf. for example N-methyl-amino acids: R. Bowmann et al. J. Chem. Soc. (1950) p. 1346; J. R. McDermott et al. Can. J. Chem. 51 (1973) p. 1915; H. Wurzinger et al., Kontakte [Catalysts] (Merck, Darmstadt) 3 (1987) p. 8; 2-halogenocarboxylic acid derivatives: S. M. Birnbaum et al. J. Amer. Chem. Soc. 76 (1954) p. 6054, C. S. Rondestvedt, Jr. et al. Org. Reactions 11 (1960) p. 189 [Review]) or can be obtained by the processes described in these publications.

Coupling reagents which are used for the coupling reaction for synthesizing the tetradepsipeptides of the formulae (II), (III) which are employed according to the invention as starting compounds are all coupling reagents which are suitable of producing an amide linkage (cf. for example Houben-Weyl, Methoden der organischen Chemie [Methods in Organic Chemistry], Volume 15/2; Bodanszky et al., Peptide Synthesis 2nd ed. (Wiley & Sons, New York 1976) or Gross, Meienhofer, The Peptides: Analysis synthesis, biology (Academic Press, New York, 1979).

The open-chain octadepsipeptides of the formula (I) which are in accordance with the invention can thus be obtained by the following reaction sequence which comprises the following steps:

a) synthesis of the didepsipeptides of the formulae (IV) to (VII):

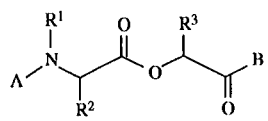 (IV)

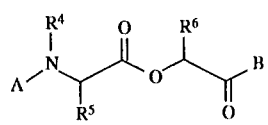 (V)

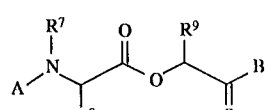 (VI)

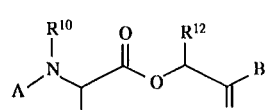 (VII)

in which A denotes an N-terminal protective group such as, for example, the benzyl or benzyloxycarbonyl group, and B denotes a C-terminal protective group such as, for example, the tert-butoxy group.

In the case of formula (IV), for example, this follows the equation below:

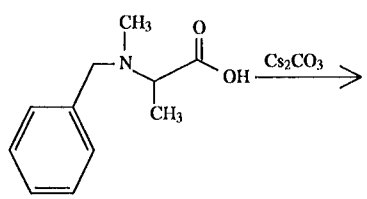 (IVa)

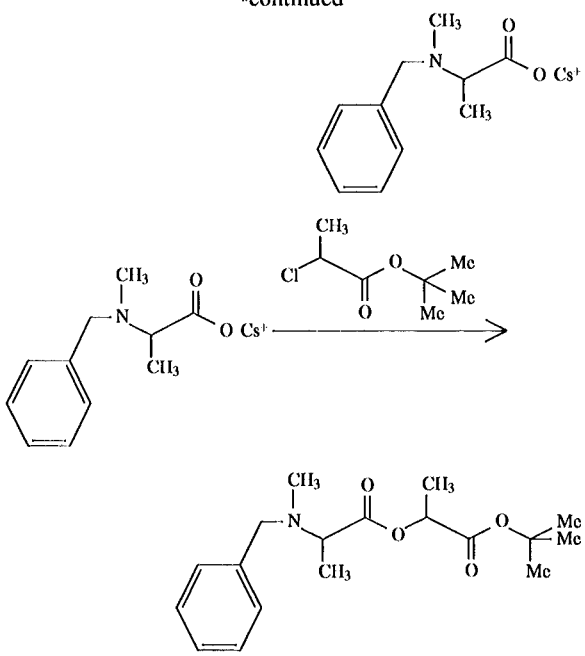

The preparation of the enantiomerically pure compounds of the formulae (IV), (V), (VI), and (VII) can, if appropriate, also be carried out via separation of the diastereomers by customary methods such as, for example, crystallization, by column chromatography or by countercurrent distribution. The best possible process will have to be decided in each individual case; sometimes it is also expedient to use combinations of the individual processes.

At the end of this step, the N-terminal protective group may be removed from the derivatives of the formula (V and VII) in a manner known per se, for example by catalytic hydrogenation, to prepare the derivatives of the formula (Va and VIIa), or elimination of the C-terminal protective group from the derivatives of the formula (IV) and (VI) may be effected in a manner known per se, preferably by acidolysis, to synthesize the derivatives (IVb) and (VIb):

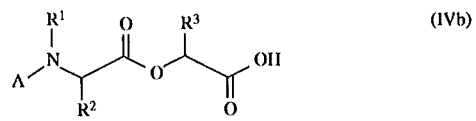 (IVb)

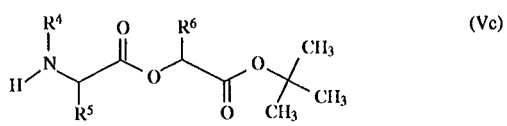 (Vc)

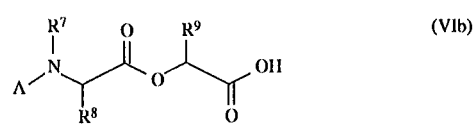 (VIb)

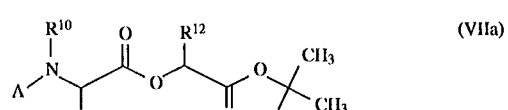 (VIIa)

b) Synthesis of the tetradepsipeptides of the formula (II) and (III)

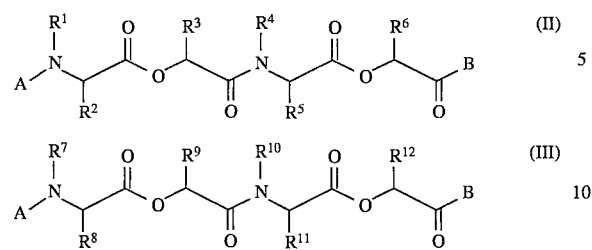

in the case of formula (IIb), this follows the equation below:

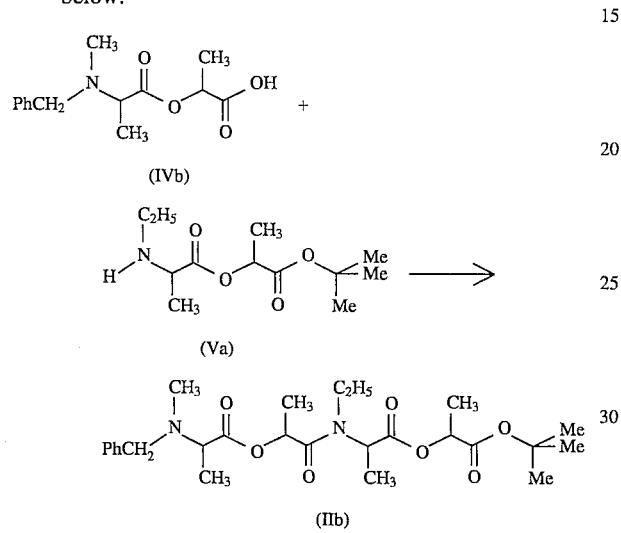

Subsequently, the N-terminal protective group may be removed from the derivatives of the formula (IIb), for example by catalytic hydrogenation, as indicated above, to prepare the derivatives of the formula

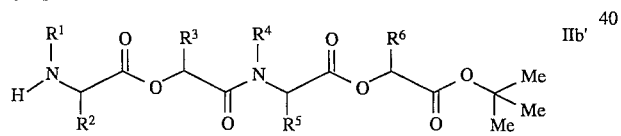

c) Synthesis of the open-chain octadepsipeptides of the formula

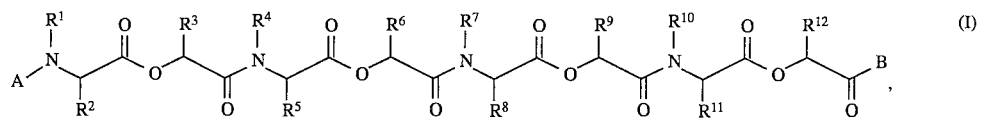

by the following equation

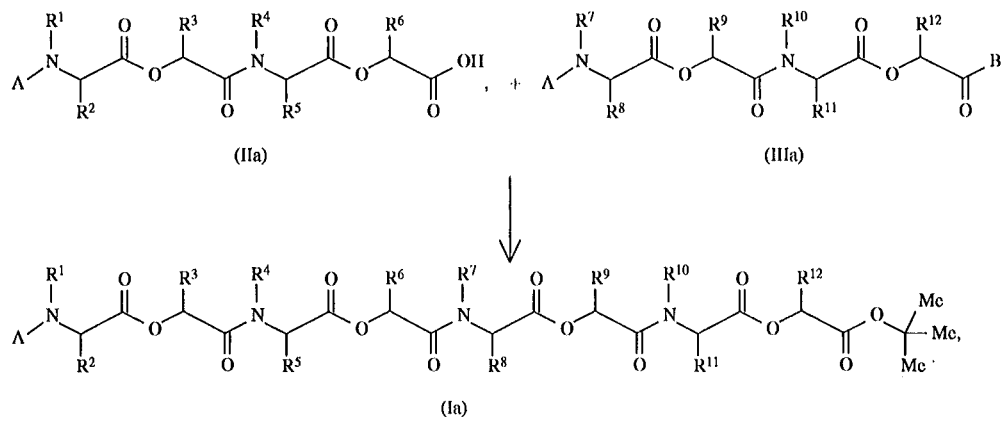

(IIa)  ,  +  (IIIa)

↓

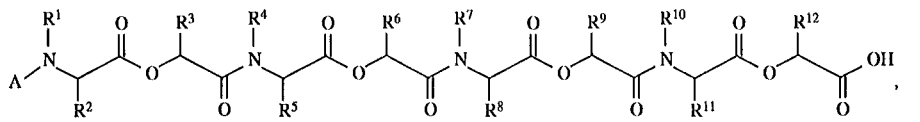

(Ia)

The C-terminal protective group may subsequently be eliminated from the derivatives of the formula (Ia) in a manner known per se, for example by acidolysis, to prepare the derivatives

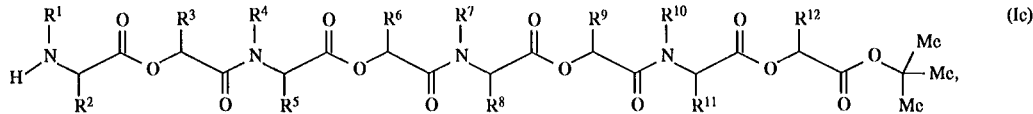

(Ib)

or the derivatives of the formula (I) are deblocked N-terminally in a manner known per se, for example by catalytic hydrogenation as indicated above, to prepare the derivatives of the formula

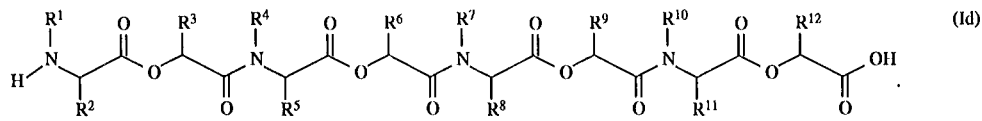

(Ic)

At the end of these steps, the N-terminal or C-terminal protective group may be eliminated from the derivatives of the formula (Ib) or (Ic), respectively, in a manner known per se, for example by catalytic hydrogenation or by acidolysis, as indicated above, to prepare the derivatives of the formula (Id)

The products obtained can be purified in the customary manner by recrystallization or column chromatography (cf. also the preparation examples).

While having low toxicity to warm-blooded species, the active compounds are suitable for combating pathogenic endoparasites which occur in humans and in animal keeping and in livestock breeding in productive livestock, breeding animals, zoo animals, laboratory animals, experimental animals and pets. In this context, they are active against all or individual stages of development of the pests and against resistant and normally-sensitive species. By combating the pathogenic endoparasites, it is intended to reduce disease, deaths and decreasing performance (for example in the production of meat, milk, wool, hides, eggs, honey etc.), so that more economical and simpler animal keeping is possible by using the active compounds. The pathogenic endoparasites include Cestodes, Trematodes, Nematodes and Acantocephala, in particular:

From the order of the Pseudophyllidea, for example: Diphyllobothrium spp., Spirometra spp., Schistocephalus spp., Ligula spp., Bothridium spp., Diphlogonoporus spp.

From the order of the Cyclophyllidea, for example: Mesocestoides spp., Anoplocephala spp., Paranoplocephala spp., Moniezia spp., Thysanosomsa spp., Thysaniezia spp., Avitellina spp., Stilesia spp., Cittotaenia spp., Andyra spp., Bertiella spp., Taenia spp., Echinococcus spp., Hydatigera spp., Davainea spp., Raillietina spp., Hymenolepis spp., Echinolepis spp., Echinocotyle spp., Diorchis spp., Dipylidium spp., Joyeuxiella spp., Diplopylidium spp.

From the subclass of the Monogenea, for example: Gyrodactylus spp., Dactylogyrus spp., Polystoma spp.

From the subclass of the Digenea, for example: Diplostomum spp., Posthodiplostomum spp., Schistosoma spp., Trichobilharzia spp., Ornithobilharzia spp., Austrobilharzia spp., Gigantobilharzia spp., Leucochloridium spp., Brachylaima spp., Echinostoma spp., Echinoparyphium spp., Echinochasmus spp., Hypoderacum spp., Fasciola spp., Fasciolides spp., Fasciolopsis spp., Cyclocoelum spp., Typhlocoelum spp., Paramphistomum spp., Calicophoron spp., Cotylophoron spp., Gigantocotyle spp., Fischoederius spp., Gastrothylacus spp., Notocotylus spp., Catatropis spp., Plagiorchis spp., Prosthogonimus spp., Dicrocoelium spp., Eurytrema spp., Troglotrema spp., Paragonimus spp., Collyriclum spp., Nanophyetus spp., Opisthorchis spp., Clonorchis spp., Metorchis spp., Heterophyes spp., Metagonimus spp.

From the order of the Enoplida, for example: Trichuris spp., Capillaria spp., Trichomosoides spp., Trichinella spp.

From the order of the Rhabditia, for example: Micronema spp., Strongyloides spp.

From the order of the Strongylida, for example: Stronylus spp., Triodontophorus spp., Oesophagodontus spp., Trichonema spp., Gyalocephalus spp., Cylindropharynx spp., Poteriostomum spp., Cyclococerus spp., Cylicostephanus spp., Oesophagostomum spp., Chabertia spp., Stephanurus spp., Ancylostoma spp., Uncinaria spp., Bunostomum spp., Globocephalus spp., Syngamus spp., Cyathostoma spp., Metastrongylus spp., Dictyocaulus spp., Muellerius spp., Protostrongylus spp., Neostrongylus spp., Cystocaulus spp., Pneumostrongylus spp., Spicocaulus spp., Elasphostrongylus spp., Parelaphostrongylus spp., Crenosoma spp., Paracrenosoma spp., Angiostrongylus spp., Aelurostrongylus spp., Filaroides spp., Parafilaroides spp., Trichostrongylus spp., Haemonchus spp., Ostertagia spp., Marshallagia spp., Cooperia spp., Nematodirus spp., Hyostrongylus spp., Obeliscoides spp., Amidostomum spp., Ollulanus spp.

From the order of the Oxyurida, for example: Oxyuris spp., Enterobius spp., Passalurus spp., Syphacia spp., Aspiculuris spp., Heterakis spp..

From the order of the Ascaridia, for example: Ascaris spp., Toxascaris spp., Toxocara spp., Parascaris spp., Anisakis spp., Ascaridia spp.

From the order of the Spirurida, for example: Gnathostoma spp., Physaloptera spp., Thelazia spp., Gongylonema spp., Habronema spp., Parabronema spp., Draschia spp., Dracunculus spp.

From the order of the Filariida, for example: Stephanofilaria spp., Parafilaria spp., Setaria spp., Loa spp., Dirofilaria spp., Litomosoides spp., Brugia spp., Wuchereria spp., Onchocerca spp..

From the order of the Gigantorhynchida, for example: Filicollis spp., Moniliformis spp., Macracanthorhynchus spp., Prosthenorchis spp..

The productive livestock and breeding animals include mammals such as, for example, cattle, horses, sheep, pigs, goats, camels, water buffalo, donkeys, rabbits, fallow deer, reindeer, fur-bearing animals such as, for example, mink, chinchilla, racoon, birds such as, for example, chickens, geese, turkeys, ducks, freshwater and salt-water fish such as, for example, trout, carps, eels, reptiles, insects such as, for example, honeybee and silkworm.

Laboratory animals and experimental animals include mice, rats, guinea pigs, golden hamsters, dogs and cats.

Pets include dogs and cats.

Administration can be effected prophylactically as well as therapeutically. The active compounds are administered, directly or in the form of suitable preparations, enterally, parenterally, dermally, nasally, by environment treastment, or with the aid of active-compound-containing shaped articles such as, for example, strips, plates, bands, collars, ear marks, limb bands, marking devices.

Internal administration is effected, for example, orally in the form of powders, tablets, capsules, pastes, drinks, granules, or solutions, suspensions and emulsions which can be administered orally, or boli, medicated feed or drinking water. Dermal administration is effected, for example, in the form of dipping, spraying or pouring-on and spotting-on. Parenteral administratioin is effected, for example, in the form of injection (intramuscularly, subcutaneously, intravenously, intraperitoneally) or by implants.

Suitable preparations are:

Solutions such as solutions for injections, oral solutions, concentrates for oral administration after dilution, solutions for use on the skin or in body cavities, pour-on and spot-on formulations, gels;

Emulsions and suspensions for oral or dermal administration and for injection; semi-solid preparations;

formulations in which the active compound is incorporated in a cream base or in an oil-in-water or water-in-oil emulsion base;

Solid preparations such as powders, premixes or concentrates, granules, pellets, tablets, boli, capsules; aerosols and inhalants, shaped articles containing active compound.

Injectable solutions are administered intravenously, intramuscularly and subcutaneously.

Injectable solutions are prepared by dissolving the active compound in a suitable solvent and, if appropriate, adding additives such as solubilizers, acids, bases, buffer salts, antioxidants and preservatives. The solutions are sterile-filtered and drawn off.

The following may be mentioned as solvents: physiologically acceptable solvents such as water, alcohols such as ethanol, butanol, benzyl alcohol, glycerol, propylene glycol, polyethylene glycols, N-methyl-pyrrolidone, and mixtures of these.

If appropriate, the active compounds can also be dissolved in physiologically acceptable vegetable or synthetic oils which are suitable for injection.

The following may be mentioned as solubilizers: solvents which enhance solution of the active compound in the main solvent, or which prevent its precipitation. Examples are polyvinylpyrrolidone, polyoxyethylated castor oil, polyoxyethylated sorbitan esters.

Preservatives are: benzyl alcohol, trichlorobutanol, p-hydroxybenzoic esters, n-butanol.

Oral solutions are administered directly. Concentrates are administered orally after previously having been diluted to the administration concentration. Oral solutions and concentrates are prepared as described above in the case of the solutions for injection, it being possible to dispense with working under sterile conditions.

Solutions for use on the skin are applied dropwise, brushed on, rubbed in, splashed on or sprayed on. These solutions are prepared as described above in the case of injectable solutions.

It may be advantageous to add thickeners during the preparation. Thickeners are: inorganic thickeners such as bentonite, colloidal silica, aluminium monostearate, organic thickeners such as cellulose derivatives, polyvinyl alcohols and their copolymers, acrylates and methacrylates.

Gels are applied to, or brushed onto, the skin, or introduced into body cavities. Gels are prepared by treating solutions which have been prepared as described in the case of the solutions for injection with such an amount of thickener that a clear substance of cream-like consistency is formed. Thickeners employed are the thickeners indicated further above.

Pour-on and spot-on formulations are poured onto, or splashed onto, limited areas of the skin, the active compound penetrating the skin and acting systemically.

Pour-on and spot-on formulations are prepared by dissolving, suspending or emulsifying the active compound in suitable solvents or solvent mixtures which are tolerated by the skin. If appropriate, other adjuvants such as colourants, resorption accelerators, antioxidants, light stabilizers, and tackifiers are added.

Solvents which may be mentioned are: water, alkanols, glycols, polyethylene glycols, polypropylene glycols, glycerol, aromatic alcohols such as benzyl alcohol, phenylethanol, phenoxyethanol, esters such as ethyl acetate, butyl acetate, benzyl benzoate, ethers such as alkylene glycol alkyl ethers such as dipropylene glycol monomethyl ether, diethylene glycol mono-butyl ether, ketones such as acetone, methyl ethyl ketone, aromatic and/or aliphatic hydrocarbons, vegetable or synthetic oils, DMF, dimethylacetamide, N-methyl-pyrrolidone, 2,2-dimethyl-4-oxy-methylene-1,3-dioxolane.

Colourants are all colourants which are released for use on animals and which can be dissolved or suspended.

Examples of resorption accelerators are DMSO, spreading oils such as isopropyl myristate, dipropylene glycol pelargonate, silicone oils, fatty acid esters, triglycerides, fatty alcohols.

Antioxidants are sulphites or metabisulphites such as potassium metabisulphite, ascorbic acid, butylhydroxytoluene, butylhydroxyanisole, tocopherol.

Examples of liquid stabilizers are novantisolic acid.

Examples of tackifiers are cellulose derivatives, starch derivatives, polyacrylates, natural polymers such as alginates, gelatine.

Emulsions can be administered orally, dermally or in the form of injections.

Emulsions are either of the water-in-oil type or of the oil-in-water type. They are prepared by dissolving the active compound either in the hydrophobic or in the hydrophilic phase and homogenizing this phase with the solvent of the other phase, with the aid of suitable emulsifiers and, if appropriate, other adjuvants such as colourants, resorption accelerators, preservatives, antioxidants, light stabilizers, viscosity-increasing substances.

The following may be mentioned as the hydrophobic phase (oils): paraffin oils, silicone oils, natural vegetable oils such as sesame seed oil, almond oil, castor oil, synthetic triglycerides such as caprylic/capric acid biglyceride, triglyceride mixture with vegetable fatty acids of chain length $C_{8-12}$ or with other specifically selected natural fatty acids, partial glyceride mixtures of saturated or unsaturated fatty acids which may also contain hydroxyl groups, and mono- and diglycerides of the $C_{8/10}$-fatty acids.

Fatty acid esters such as ethyl stearate, di-n-butyryl adipate, hexyl laurate, dipropylene glycol pelargonate, esters of a branched fatty acid of medium chain length with saturated fatty alcohols of chain length $C_{16-18}$, isopropyl myristate, isopropyl palmitate, caprylic/capric esters of saturated fatty alcohols of chain length $C_{12}$–$C_{18}$, isopropyl stearate, oleyl oleate, decyl oleate, ethyl oleate, ethyl lactate, waxy fatty acid esters such as artificial uropygial gland fat from ducks, dibutyl phthalate, diisopropyl adipate, ester mixtures related to the latter, etc.

Fatty alcohols such as isotridecyl alcohol, 2-octyldodecanol, cetylstearyl alcohol, oleyl alcohol.

Fatty acids such as, for example, oleic acid and its mixtures.

The following may be mentioned as hydrophilic phase: water, alcohols such as, for example, propylene glycol, glycerol, sorbitol and their mixtures.

The following may be mentioned as emulsifiers: nonionic surfactants, for example polyoxyethylated castor oil, polyoxyethylated sorbitan monooleate, sorbitan monostearate, glycerol monostearate, polyoxyethyl stearate, alkylphenol polyglycol ethers;

ampholytic surfactants such as disodium N-lauryl-β-iminodipropionate or lecithin; anionic surfactants such as sodium lauryl sulphate, fatty alcohol ether sulphates, the monoethynolamine salt of mono/dialkylpolyglycol ether orthophosphoric esters;

The following may be mentioned as other adjuvants: viscosity-increasing substances and substances which stabilize the emulsion, such as carboxymethylcellulose, methylcellulose and other cellulose and starch derivatives, polyacrylates, alginates, gelatine, gum arabic, polyvinylpyrrolidone, polyvinyl alcohol, copolymers of methyl vinyl ether and maleic anhydride, polyethylene glycols, waxes, colloidal silica, or mixtures of the substances mentioned.

Suspensions can be administered orally, dermally or in the form of injection. They are prepared by suspending the active compound in an excipient liquid, if appropriate with the addition of further adjuvants such as wetting agents, colourants, resorption accelerators, preservatives, antioxidants light stabilizers.

Excipient liquids which may be mentioned are all homogeneous solvents and solvent mixtures.

Wetting agents (dispersants) which may be mentioned are the surfactants indicated further above.

Further adjuvants which may be mentioned are those indicated further above.

Semi-solid preparations can be administered orally or dermally. They are only distinguished from the above-described suspensions and emulsions by their higher viscosity.

To prepare solid preparations, the active compound is mixed with suitable excipients, if appropriate with the addition of adjuvants, and the mixture is formulated as desired.

Excipients which may be mentioned are all physiologically acceptable solid inert substances. Suitable as such are inorganic and organic substances. Examples of inorganic substances are sodium chloride, carbonates such as calcium carbonate, hydrogen carbonates, aluminium oxides, silicas, clays, precipitated or colloidal silicon dioxide, and phosphates.

Examples of organic substances are sugars, cellulose, foods and animal feeds such as dried milk, carcass meals, cereal meals and coarse-cereal meals and starches.

Adjuvants are preservatives, antioxidants and colourants which have already been indicated further above.

Other suitable adjuvants are lubricants and gliding agents such as, for example, magnesium stearate, stearic acid, talc, bentonites, disintegrants such as starch or crosslinked polyvinylpyrrolidone, binders such as, for example, starch, gelatine or linear polyvinylpyrrolidone, and also dry binders such as microcrystalline cellulose.

In the preparations, the active compounds can also be present in the form of a mixture with synergists or with other active compounds which act against pathogenic endoparasites. Examples of such active compounds are L-2,3,5,6-tetrahydro-6-phenylimidazothiazole, benzimidazole carbamates, praziquantel, pyrantel, febantel.

Ready-to-use preparations contain the active compound in concentrations of 10 ppm–20 percent by weight, preferably of 0.1–10 percent by weight.

Preparations which are diluted prior to administration contain the active compound in concentrations of 0.5–90% by weight, preferably of 5–50% by weight.

In general, it has proved advantageous to administer amounts of approximately 1 to approximately 100 mg of active compound per kg of body weight per day to achieve effective results.

EXAMPLE A

In vivo nematode test Haemonchus contortus/sheep

Sheep which had been infected experimentally with Haemonchus contortus were treated after the prepatency period of the parasite had elapsed. The active compounds were applied orally and/or intravenously in the form of the pure active compound.

The degree of effectiveness is determined by quantitatively determinating the nematode eggs excreted with the faeces before and after the treatment.

If egg excretion has stopped completely after the treatment, this means that the nematodes were aborted or are damaged to such an extent that they no longer produce eggs (dosis effectiva).

Active compounds which were tested under effective dosage rates (dosis effectiva) can be seen from the table which follows:

| Active compound Example No. | Dosis effectiva in mg/kg |
|---|---|
| 1 | 10 |
| 2 | 10 |
| 3 | 10 |

Preparation Examples

Example 1 tert-Butyl-N-benzyl-N-methyl-L-leucyl-D-lactyl-N-Methyl-L-leucyl-D-3-phenyllactyl-N-methyl-L-leucyl-D-lactyl-N-methyl-L-leucyl-D-3-phenyllactate H-L-MeLeu-D-Lac-L-MeLeu-D-PheLac-O$^t$Bu (1.38 g, 2.52 mmol) and Bzl-L-MeLeu-D-Lac-L-MeLeu-D-PheLac-OH (1.46 g, 2.52 mmol) were introduced into dichloromethane (15 ml), and ethyldiisopropylamine (158.9 μl, 0.912 mmol) and BOP-Cl (111.5 mg, 0.438 mmol) were added to the solution which had been cooled to 0° C. Stirring was continued for 1 hour at 0° C. and for 1.5 hours at room temperature, and the mixture was then diluted with dichloromethane, washed twice with a small quantity of water, dried over sodium sulphate and concentrated. Flash chromatography of the residue on silica gel using cyclohexane/$^t$BuOMe=2:1 as the eluent gave 2.18 g (79%) of Bzl-L-MeLeu-D-Lac-L-MeLeu-D-PheLac-L-MeLeu-D-Lac-L-MeLeu-D-PheLac-O$^t$Bu.

FAB-MS m/z (%): 1113 (M$^+$+H, 100), 1023 (8), 909 (6), 710 (16).

EXAMPLE 2 tert-Butyl-N-Benzyl-N-propyl-L-leucyl-D-lactyl-N-$^i$-propyl-L-leucyl-D-3-phenyllactyl-N-$^i$propyl-L-leucyl-D-lactyl-N-$^i$propyl-L-leucyl-D-3-phenyllactate H-L-$^i$PrLeu-D-Lac-L-$^i$PrLeu-D-PheLac-O$^t$Bu (4.05 g, 6.69 mmol) and Bzl-L-$^i$PrLeu-D-Lac-L-$^i$PrLeu-D-PheLac-OH (4.48 g, 7.02 mmol) were introduced into dioxane (150 ml), and ethyl diisopropylamine (2.16 g, 16.73 mmol) and BOP-Cl (2.04 g, 8.03 mmol) were added to the solution which had been cooled to 0° C. The mixture was refluxed for 30 hours, cooled, concentrated and taken up in dichloromethane. This was washed twice with a small quantity of water, dried over sodium sulphate and concentrated. Flash chromatography of the residue on silica gel using $^t$BuOMe-cyclohexane=1:5 as the eluent gave 3.2 g (39%) of Bzl-L-$^i$PrLeu-D-Lac-L-$^i$PrLeu-D-PheLac-$^i$PrLeu-D-Lac-L-$^i$PrLeu-D-PheLac-O$^t$Bu.

FAB-MS m/z (%): 1225 (68, M$^+$), 218 (100).

EXAMPLE 3

H-L-MePhe-D-Lac-L-MePhe-D-PheLac-O$^t$Bu (1.96 g, 3.19 mmol) and Bzl-L-MePhe-D-Lac-L-MePhe-D-PheLac-OH (2.18 g, 3.35 mmol) were introduced into dichloromethane (20 ml), and ethyldiisopropylamine (1.03 g, 7.97 mmol) were added to the solution which had been cooled to 0° C. The mixture was stirred for 12 hours at room temperature, washed twice with a small amount of saturated NaHCO$_3$ solution, dried over sodium sulphate and concentrated. Flash chromatography of the residue on silica gel using cyclohexane-ethyl acetate=4:1 as the eluent gave 3.5 g (89%) of Bzl-L-MePhe-D-Lac-L-MePhe-D-PheLac-MePhe-D-Lac-L-MePhe-D-PheLac-O$^t$Bu.

FAB-MS m/z (%): 1249 (84, M$^+$), 712 (43), 224 (100).

The compounds of the general formula (I) which are listed in table 2 below can be prepared analogously in the form of the LDLDLDLD stereoisomers.

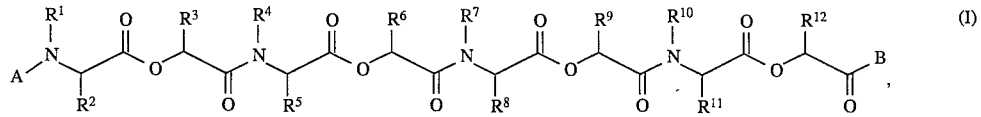

TABLE 2

| Ex. No. | A | R$^1$ | R$^2$ | R$^3$ | R$^4$ | R$^5$ | R$^6$ | R$^7$ | R$^8$ | R$^9$ | R$^{10}$ | R$^{11}$ | R$^{12}$ | B | Mass spectroscopy data FAB-MS m/z (%) |
|---|---|---|---|---|---|---|---|---|---|---|---|---|---|---|---|
| 4 | Bzl | Me | $^i$Bu | Me | Me | $^i$Bu | Bzl | Me | $^i$Bu | Me | Me | $^i$Bu | Bzl | OH | 1057 (70, (M + H)$^{+)}$ |
| 5 | Bzl | Me | $^i$Pr | Me | Me | $^i$Pr | Bzl | Me | $^i$Pr | Me | Me | $^i$Pr | Bzl | O$^t$Bu | 1057 (100, (M + H)$^{+)}$ |
| 6 | Bzl | Me | $^s$Bu | Me | Me | $^s$Bu | Bzl | Me | $^s$Bu | Me | Me | $^s$Bu | Bzl | O$^t$Bu | 1113 (78, (M + H)$^{+)}$ |
| 7 | Bzl | Me | $^i$Pr | Me | Me | $^i$Pr | Bzl | Me | $^i$Pr | Me | Me | $^i$Pr | Bzl | OH | |

TABLE 2-continued

| Ex. No. | A | R¹ | R² | R³ | R⁴ | R⁵ | R⁶ | R⁷ | R⁸ | R⁹ | R¹⁰ | R¹¹ | R¹² | B | Mass spectroscopy data FAB-MS m/z (%) |
|---|---|---|---|---|---|---|---|---|---|---|---|---|---|---|---|
| 8  | Bzl | Me  | sBu | Me | Me  | sBu | Bzl      | Me  | sBu | Me | Me  | sBu | Bzl      | OH  |                       |
| 9  | Bzl | Pr  | iBu | Me | Pr  | iBu | Bzl      | Pr  | iBu | Me | Pr  | iBu | Bzl      | OtBu | 1225 (26, (M+H)[1])  |
| 10 | Bzl | Et  | iBu | Me | Et  | iBu | Bzl      | Et  | iBu | Me | Et  | iBu | Bzl      | OtBu | 1169 (30, (M+H)[1])  |
| 11 | H   | Me  | iPr | Me | Me  | iPr | Bzl      | Me  | iPr | Me | Me  | iPr | Bzl      | OH   | 911 (100, (M+H)[1])  |
| 12 | H   | Me  | sBu | Me | Me  | sBu | Bzl      | Me  | sBu | Me | Me  | sBu | Bzl      | OH   | 967 (100, (M+H)[1])  |
| 13 | Bzl | iPr | iBu | Me | iPr | iBu | Bzl      | iPr | iBu | Me | iPr | iBu | Bu       | OH   | 1169 (100, (M+H)[1]) |
| 14 | Bzl | Me  | Bzl | Me | Me  | Bzl | Bzl      | Me  | Bzl | Me | Me  | Bzl | Bzl      | OH   | 1193 (64, (M+H)[1])  |
| 15 | H   | Me  | Bzl | Me | Me  | Bzl | Bzl      | Me  | Bzl | Me | Me  | Bzl | Bzl      | OH   | 1103 (100, (M+H)[1]) |
| 16 | Bzl | Me  | iBu | Me | Me  | iBu | p-Cl-Bzl | Me  | iBu | Me | Me  | iBu | p-Cl-Bzl | OtBu | 1181 (42, M⁺)        |
| 17 | H   | Me  | iBu | Me | Me  | iBu | p-Cl-Bzl | Me  | iBu | Me | Me  | iBu | p-Cl-Bzl | OtBu | 1091 (100, M⁺)       |
| 18 | Bzl | Me  | Me  | Me | Me  | Me  | Bzl      | Me  | Me  | Me | Me  | Me  | Bzl      | OtBu | 945 (17, (M+H)[1])   |
| 19 | H   | Me  | Me  | Me | Me  | Me  | Bzl      | Me  | Me  | Me | Me  | Me  | Bzl      | OtBu | 855 (98, (M+H)[1])   |
| 20 | Bzl | Me  | Me  | Me | Me  | Me  | Bzl      | Me  | iBu | Me | Me  | iBu | Bzl      | OtBu | 1029 (12, (M+H)[1])  |
| 21 | H   | Me  | Me  | Me | Me  | Me  | Bzl      | Me  | iBu | Me | Me  | iBu | Bzl      | OtBu | 939 (100, (M+H)[1])  |
| 22 | H   | Me  | Me  | Me | Me  | Me  | Bzl      | Me  | iBu | Me | Me  | iBu | Bzl      | OH   | 883 (100, (M+H)[1])  |

Examples of the preparation of the starting substances of the formulae (II) and (III)

Example II-1 tert-Butyl-N-benzyl-N-methyl-L-leucyl-D-lactyl-N-methyl-L-leucyl-D-3-phenyllactate The coupling reaction is carried out analogously to the reaction protocol of Example 1, but

| | |
|---|---|
| 8.0 g (22.9 mmol) of | L-McLeu-D-Lac-L-McLeu-D-PheLac-OtBu, |
| 8.44 g (27.5 mmol) of | Bzl-L-McLeu-D-Lac-L-McLeu-D-PheLac-OH, |
| 80 ml | of dichloromethane, |
| 9.98 ml (57.3 mmol) | of diisopropylethylamine |
| 7.59 g (29.8 mmol) | of bis-(2-oxo-3-oxazolidinyl)-phosphinic chloride | are used.

Flash chromatography of the residue on silica gel using cyclohexane/ethyl acetate=15:1 gave 11.6 g (80%) of Bzl-L-McLeu-D-Lac-L-McLeu-D-PheLac-L-McLeu-D-PheLac-D-OtBu.

FAB-MS m/z (%): 639 (37, (M+H), 199 (100).

Example II-2

N-Benzyl-N-methyl-L-leucyl-D-lactyl-N-methyl-L-leucyl-D-3-phenyllactic acid

HCl gas was passed for 2 hours through a solution of Bzl-L-McLeu-D-Lac-L-McLeu-D-PheLac-OtBu (5.46 g, 8.56 mmol) in dichloromethane (150 ml), cooled to 0° C. The mixture was subsequently heated to room temperature and stirred overnight. It was concentrated and twice taken up in dichloromethane and then again evaporated on a rotary evaporator. The acid which was dissolved in water/methanol=1:1 (100 ml) was stirred for 4 hours with basic ion exchanger (15 g). After filtration, concentration and drying under a high vacuum, 4.1 g (80%) of Bzl-L-McLeu-D-Lac-L-McLeu-D-PheLac-OH was obtained.

FAB-MS m/z (%): 583 (100 (M+H), 190 (64).

Example III-1 tert-butyl-N-methyl-L-leucyl-D-lactyl-N-methyl-L-leucyl-D-3-phenyllactic acid

Bzl-L-McLeu-D-Lac-L-McLeu-D-PheLac-OtBu (6.08 g 9.53 mmol) was dissolved in ethanol (37 ml) 0.6 g of Pd(OH)₂/C (20%) was added, and the mixture was hydrogenated at room temperature until hydrogen was no longer taken up. After the catalyst had been filtered off and the solvent had been concentrated, separation of the residue by column chromatography on silica gel using tBuOMe-cyclohexane-ethanol=1:1:0.05 as the eluent gave 3.87 g (74%) of L-McLeu-DLac-L-McLeu-D-PheLac-OtBu.

FAB-MS m/z (%): 549 (100, (M+H), 493 (58).

The compounds listed in Table 3 below can be prepared analogously in the form of the LDLD stereoisomers.

TABLE 3

$$R^1\text{-N}(A)\text{-CH}(R^2)\text{-C(O)-O-CH}(R^3)\text{-C(O)-N}(R^4)\text{-CH}(R^5)\text{-C(O)-O-CH}(R^6)\text{-C(O)-B}$$

| Ex. No. | A | $R^1$ | $R^2$ | $R^3$ | $R^4$ | $R^5$ | $R^6$ | B | Mass spectroscopy data MS |
|---|---|---|---|---|---|---|---|---|---|
| II-3 | Bzl | Me | $^i$Pr | Me | Me | $^i$Pr | Bzl | O$^t$Bu | 611 (60, M$^+$) |
| II-4 | Bzl | Me | $^s$Bu | Me | Me | $^s$Bu | Bzl | O$^t$Bu | 639 (82, (M + H)$^+$) |
| II-5 | H | Me | $^i$Pr | Me | Me | $^i$Pr | Bzl | O$^t$Bu | 521 (100, (M + H)$^+$) |
| II-6 | H | Me | $^s$Bu | Me | Me | $^s$Bu | Bzl | O$^t$Bu | 549 (70, (M + H)$^+$) |
| II-7 | H | Me | $^i$Bu | Me | Me | $^i$Bu | Bzl | O$^t$Bu | 548 (100, (M + H)$^+$) |
| II-8 | Bzl | Pr | $^i$Bu | Me | Pr | $^i$Bu | Bzl | O$^t$Bu | 695 (76, (M + H)$^+$) |
| II-9 | Bzl | Et | $^i$Bu | Me | Et | $^i$Bu | Bzl | O$^t$Bu | 667 (22, (M + H)$^+$) |
| II-10 | Bzl | $^i$Pr | $^i$Bu | Me | $^i$Pr | $^i$Bu | Bzl | O$^t$Bu | 695 (18, (M + H)$^+$) |
| II-11 | H | Pr | $^i$Bu | Me | Pr | $^i$Bu | Bzl | O$^t$Bu | 605 (96, (M + H)$^+$) |
| II-12 | H | Et | $^i$Bu | Me | Et | $^i$Bu | Bzl | O$^t$Bu | 577 (69, (M + H)$^+$) |
| II-13 | Bzl | Pr | $^i$Bu | Me | Pr | $^i$Bu | Bzl | OH | 639 (30, (M + H)$^+$) |
| II-14 | Bzl | Et | $^i$Bu | Me | Et | $^i$Bu | Bzl | OH | 611 (32, (M + H)$^+$) |
| II-15 | Bzl | $^i$Pr | $^i$Bu | Me | $^i$Pr | $^i$Bu | Bzl | OH | 639 (70, (M + H)$^+$) |
| II-16 | H | $^i$Pr | $^i$Bu | Me | $^i$Pr | $^i$Bu | Bzl | O$^t$Bu | 605 (100, M$^+$) |
| II-17 | Bzl | Me | Bzl | Me | Me | Bzl | Bzl | O$^t$Bu | 707 (18, M$^+$) |
| II-18 | H | Me | Bzl | Me | Me | Bzl | Bzl | O$^t$Bu | 617 (36, (M + H)$^+$) |
| II-19 | Bzl | Me | Bzl | Me | Me | Bzl | Bzl | OH | 651 (68, (M + H)$^+$) |
| II-20 | H | Pr | $^i$Pr | Me | Pr | $^i$Bu | Bzl | OH | |
| II-21 | Bzl | Me | $^i$Bu | Me | Me | $^i$Bu | p-Cl—Bzl | O$^t$Bu | 673 (100, (M + H)$^+$) |
| II-22 | H | Me | $^i$Bu | Me | Me | $^i$Bu | p-Cl—Bzl | O$^t$Bu | 583 (22, (M + H)$^+$) |
| II-23 | Bzl | Me | $^i$Bu | Me | Me | $^i$Bu | p-Cl—Bzl | OH | 617 (44, (M + H)$^+$) |
| II-24 | Bzl | Me | Me | Me | Me | Me | Bzl | OH | 555 (100, (M + H)$^+$) |
| II-25 | H | Me | Me | Me | Me | Me | Bzl | O$^t$Bu | |
| II-26 | Bzl | Me | Me | Me | Me | Me | Bzl | OH | 499 (10, (M + H)$^+$) |
| II-27 | Bzl | Me | Pr | Me | Me | Pr | Bzl | O$^t$Bu | 611 (100 (M + H)$^+$) |

Examples of the preparation of the starting compounds of the formula (IV) and (V)

Example (IV-1)

tert-Butyl-N-benzyl-N-methyl-L-leucyl-D-lactate

The caesium salt (77.7 g, 0.212 mol) of Bzl-L-MeLeu-OH was introduced into dimethyl sulphoxide (530 ml), and tert-Butyl-2-chloro-propionate (34.76 g, 0.212 mol) were added at room temperature. The mixture was stirred for 20 hours at room temperature, poured into saturated sodium chloride solution and extracted four times using ethyl acetate. The combined organic extracts were washed once using a small amount of water, dried over sodium sulphate and concentrated. Column chromatography of the residue on silica gel using cyclohexane/ethyl acetate=60:1 as the eluent gave 63.5 g (82%) of Bzl-MeLeu-D-Lac-O$^t$Bu.

EI-MS m/z (%): 363 (M$^+$,1), 190 (100).

Example (V-1)

tert-butyl-N-benzyl-N-methyl-L-leucyl-D-3-phenyllactate

Bzl-L-MeLeu-OH (50.0 g, 0.212 mol) was dissolved in ethanol (1000 ml) and water (100 ml), a 20% caesium carbonate solution (41.5 g, 0.12 mol) in water was added, and the mixture was stirred for 5 hours at room temperature. The mixture was subsequently concentrated, the residue was distilled twice using in each case 250 ml of DMF, and the product was dried overnight at 80° C. under a high vacuum. The caesium salt (77.7 g, 0.212 mol) was introduced into dimethyl sulphoxide (530 ml), tert-butyl 2-chloro-3-phenylpropionate (51.0 g, 0.212 mol) was added at room temperature, and the mixture was stirred for 20 hours at room temperature. The solution was poured into saturated sodium chloride solution, extracted four times using ethyl acetate, dried over sodium sulphate and concentrated. Column chromatography of the residue on silica gel using cyclohexane/ethyl acetate=100:1 as the eluent gave 26.6 g (29%) of pure Bzl-L-MeLeu-D-PheLac-O$^t$Bu and 48.9 g (52%) of a mixed fraction contaminated with tert-butyl cinnamate.

EI-MS m/z (%): 363 (1), 190 (100).

The compounds listed in table 4 below can be prepared analogously in the form of the L-D stereoisomers.

TABLE 4

![structure]

| Ex. No. | A | $R^1$ | $R^2$ | $R^3$ | B | Mass spectroscopy data |
|---|---|---|---|---|---|---|
| IV-2 | Bzl | Me | —(CH$_2$)$_2$—S—Me | Bzl | O$^t$Bu | 458 (100, (M+H)$^+$) |
| IV-3 | Bzl | Me | —(CH$_2$)$_2$—S—Me | Me | O$^t$Bu | 382 (100, (M+H)$^+$) |
| IV-4 | Bzl | Me | Pr | Me | OH | 294 (100, (M+H)$^+$) |
| IV-5 | H | Me | Pr | Bzl | O$^t$Bu | 336 8100, (M+H)$^+$) |
| IV-6 | Bzl | Me | Pr | Bzl | O$^t$Bu | 425 (2, M$^+$) |
| IV-7 | Bzl | Me | Pr | Me | O$^t$Bu | 349 (5, M$^+$) |
| IV-8 | H | Me | Me | Bzl | O$^t$Bu | 308 (100, (M+H)$^+$) |
| IV-9 | Bzl | Me | Me | Bzl | O$^t$Bu | 398 (100, M+H)$^+$) |
| IV-10 | Bzl | Me | Me | Me | O$^t$Bu | 322 (100, (M+H)$^+$) |
| IV-11 | Bzl | Me | Me | Me | OH | 265 (2, M$^+$) |
| IV-12 | H | Me | $^i$Bu | p-Cl—Bzl | O$^t$Bu | 386 (100, (M+H)$^+$) |
| IV-13 | H | Me | $^i$Bu | p-Cl—Bzl | O$^t$Bu | 384 (36, (M+H)$^+$) |
| IV-14 | Bzl | Et | $^i$Bu | Me | OH | 322 (46, (M+H)$^+$) |
| IV-15 | Bzl | $^i$Pr | $^i$Bu | Me | OH | 336 (100, (M+H)$^+$) |
| IV-16 | Bzl | Pr | $^i$Bu | Me | OH | 336 (100, (M+H)$^+$) |
| IV-17 | H | Et | $^i$Bu | Bzl | O$^t$Bu | 363 (0.5, M$^+$) |
| IV-18 | H | $^i$Pr | $^i$Bu | Bzl | O$^t$Bu | |
| IV-19 | H | Pr | $^i$Bu | Bzl | O$^t$Bu | 377 (0.4, M$^+$) |
| IV-20 | Bzl | Et | $^i$Bu | Bzl | O$^t$Bu | 454 (100, (M+H)$^+$) |
| IV-21 | Bzl | $^i$Pr | $^i$Bu | Bzl | O$^t$Bu | 467 (1, M$^+$)$^+$ |
| IV-22 | Bzl | Pr | $^i$Bu | Bzl | O$^t$Bu | 468 (100, (M+H)$^+$) |
| IV-23 | Bzl | Et | $^i$Bu | Me | O$^t$Bu | 378 (100, (M+H)$^+$) |
| IV-24 | Bzl | $^i$Pr | $^i$Bu | Me | O$^t$Bu | 392 (100, (M+H)$^+$) |
| IV-25 | Bzl | Pr | $^i$Bu | Me | O$^t$Bu | 317 (46), 260 (42), 139 (100) |
| IV-26 | H | Me | Bzl | Bzl | O$^t$Bu | 383 (6) M$^+$) |
| IV-27 | Bzl | Me | Bzl | Bzl | O$^t$Bu | 400 (2), 382 (50, 326 (36), 224 (75) |
| IV-28 | H | Me | $^s$Bu | Bzl | O$^t$Bu | 276 (6), 236 (15), 100 (100) |
| IV-29 | Bzl | Me | $^s$Bu | Me | OH | 307 (1, M$^+$) |
| IV-30 | Bzl | Me | $^i$Pr | Me | OH | 293 (2, M$^+$) |
| IV-31 | Bzl | Me | Bzl | Me | OH | 341 (1, M$^+$) |
| IV-32 | H | Me | $^i$Pr | Bzl | O$^t$Bu | |
| IV-33 | Bzl | Me | $^s$Bu | Me | O$^t$Bu | 363 (1, M$^+$) |
| IV-34 | Bzl | Me | $^s$Bu | Bzl | O$^t$Bu | 439 (2, M$^+$) |
| IV-35 | Bzl | Me | $^i$Pr | Me | O$^t$Bu | 349 (3, M$^+$) |
| IV-36 | Bzl | Me | $^i$Pr | Bzl | O$^t$Bu | 425 (1, M$^+$) |
| IV-37 | Bzl | Me | Bzl | Me | O$^t$Bu | 397 (0.5, M$^+$) |

List of abbreviations:
Leu represents leucine
Lac represents lactic acid
PheLac represents phenyllactic acid
Bzl represents benzyl
Me represents methyl
BOP—Cl represents bis-(2-oxo-3-oxazolidinyl)-phos-phonyl chloride)
$^t$Bu represents tertiary butyl
$^i$Pr represents isopropyl
$^s$Bu represents secondary butyl
Phe for for phenylalanine
Et represents ethyl
Pr represents propyl

We claim:

1. A method of combating endoparasites in a patient which comprises administering to such patient an endoparasiticidally effective amount of an open-chain octadepsipeptide of the formula

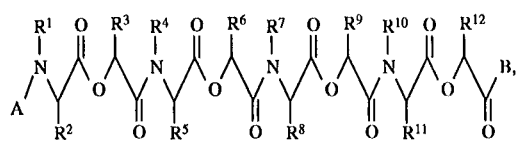

in which

A represents hydrogen, alkyl, aralkyl or an acyl radical of the formula —CO—$R^{15}$ in which $R^{15}$ represents straight-chain or branched alkyl, alkenyl, alkoxy, aralkyl or arylalkoxy having up to 6 carbon atoms in the alkyl moiety, $R^1$, $R^4$, $R^7$ and $R^{10}$ independently of one another represent $C_1$-$C_8$-alkyl, $C_3$-$C_6$-cycloalkyl or aralkyl, $R^2$, $R^5$, $R^8$ and $R^{11}$ independently of one another represent hydrogen, straight-chain or branched alkyl having up to 8 carbon atoms, hydroxyalkyl, alkanoyloxyalkyl, alkoxyalkyl, aryloxyalkyl, mercaptoalkyl, alkylthioalkyl, alkylsulphinylalkyl, alkylsulphonylalkyl, carboxyalkyl, alkoxycarbonylalkyl, arylalkoxycarbonylalkyl, carbamoylalkyl, aminoalkyl, alkylaminoalkyl, dialkylaminoalkyl, guanidinoalkyl, which itself is optionally substituted by one or two benzyloxycarbonyl radicals or by one, two, three or four alkyl radicals, or represent alkoxycarbonylaminoalkyl, 9-fluorenylmethoxycarbonyl(Fmoc)aminoalkyl, alkenyl, cycloalkyl, cycloalkylalkyl and optionally substituted arylalkyl, wherein the substituents are halogen, hydroxyl, alkyl and alkoxy, $R^3$, $R^6$, $R^9$ and $R^{12}$ independently of one another represent hydrogen, straight-chain or branched alkyl having up to 8 carbon atoms, hydroxyalkyl, alkanoyloxyalkyl, alkoxyalkyl, aryloxyalkyl, alkylthioalkyl, alkylsulphinylalkyl, alkylsulphonylalkyl, carboxyalkyl, alkoxycarbonylalkyl, arylalkoxycarbonylalkyl, carbamoylalkyl, aminoalkyl, alkylaminoalkyl, dialkyl-aminoalkyl, alkoxycarbonylaminoalkyl, alkenyl, cycloalkylalkyl, and furthermore represents aryl, aralkyl or heteroarylmethyl wherein said aryl, aralkyl or heteroarylmethyl moieties are optionally substituted by halogen, hydroxyl, $C_{1-4}$-alkyl, $C_{1-4}$-alkoxy, nitro or a $NR^{16}R^{17}$ group in which $R^{16}$ and $R^{17}$ independently from each other represent hydrogen or alkyl or together with the adjoining nitrogen atom forms a 5, 6 or 7-membered ring which is optionally interrupted by O, S or N, and said ring is optionally $C_{1-4}$ alkyl substituted, B represents hydroxyl, alkoxy having up to 4 carbon atoms or the radical $NR^{13}R^{14}$ in which $R^{13}$ and $R^{14}$ represent hydrogen, alkyl, aralkyl or aryl, or an optical isomer or racemate thereof.

2. A process for the preparation of endoparasiticidal composition which comprises mixing an octadepsipeptide of the formula

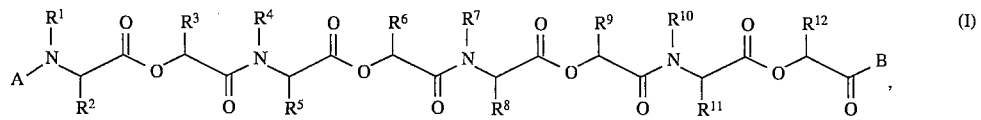

in which

A represents hydrogen, alkyl, aralkyl or an acyl radical of the formula —CO—$R^{15}$ in which $R^{15}$ represents straight-chain or branched alkyl, alkenyl, alkoxy, aralkyl or arylalkoxy having up to 6 carbon atoms in the alkyl moiety, $R^1$, $R^4$, $R^7$ and $R^{10}$ independently of one another represent $C_1$–$C_8$-alkyl, $C_3$–$C_6$-cycloalkyl or aralkyl, $R^2$, $R^5$, $R^8$ and $R^{11}$ independently of one another represent hydrogen, straight-chain or branched alkyl having up to 8 carbon atoms, hydroxyalkyl, alkanoyloxyalkyl, alkoxyalkyl, aryloxyalkyl, mercaptoalkyl, alkylthioalkyl, alkylsulphinylalkyl, alkylsulphonylalkyl, carboxyalkyl, alkoxycarbonylalkyl, arylalkoxycarbonylalkyl, carbamoylalkyl, aminoalkyl, alkylaminoalkyl, dialkylaminoalkyl, guanidinoalkyl, which itself is optionally substituted by one or two benzyloxycarbonyl radicals or by one, two, three or four alkyl radicals, or represent alkoxycarbonylaminoalkyl, 9-fluorenylmethoxycarbonyl(Fmoc)aminoalkyl, alkenyl, cycloalkyl, cycloalkylalkyl and optionally substituted arylalkyl, wherein the substituents are halogen, hydroxyl, alkyl and alkoxy, $R^3$, $R^6$, $R^9$ and $R^{12}$ independently of one another represent hydrogen, straight-chain or branched alkyl having up to 8 carbon atoms, hydroxyalkyl, alkanoyloxyalkyl, alkoxyalkyl, aryloxyalkyl, alkylthioalkyl, alkylsulphinylalkyl, alkylsulphonylalkyl, carboxyalkyl, alkoxycarbonylalkyl, arylalkoxycarbonylalkyl, carbamoylalkyl, aminoalkyl, alkylaminoalkyl, dialkyl-aminoalkyl, alkoxycarbonylaminoalkyl, alkenyl, cycloalkylalkyl, and furthermore represents aryl, aralkyl or heteroarylmethyl wherein said aryl, aralkyl or heteroarylmethyl moieties are optionally substituted by halogen, hydroxyl, $C_{1-4}$-alkyl, $C_{1-4}$-alkoxy, nitro or a $NR^{16}R^{17}$ group in which $R^{16}$ and $R^{17}$ independently from each other represent hydrogen or alkyl or together with the adjoining nitrogen atom forms a 5, 6 or 7-membered ring which is optionally interrupted by O, S or N, and said ring is optionally $C_{1-4}$ alkyl substituted, B represents hydroxyl, alkoxy having up to 4 carbon atoms or the radical $NR^{13}R^{14}$ in which $R^{13}$ and $R^{14}$ represent hydrogen, alkyl, aralkyl or aryl, with an extender and/or a surfactant.

* * * * *